United States Patent
Segermark et al.

(10) Patent No.: US 6,312,377 B1
(45) Date of Patent: Nov. 6, 2001

(54) SOFT TISSUE COMPRESSION SHIELD AND METHOD OF RETRACTING TISSUE

(75) Inventors: James Segermark, Gem Lake; Christopher Herman, White Bear Lake, both of MN (US); James Fonger, McLean, VA (US)

(73) Assignee: ViaMedics, LLC, St. Paul, MN (US)

( * ) Notice: Subject to any disclaimer, the term of this patent is extended or adjusted under 35 U.S.C. 154(b) by 0 days.

(21) Appl. No.: 09/633,430

(22) Filed: Aug. 7, 2000

Related U.S. Application Data

(60) Provisional application No. 60/195,229, filed on Apr. 6, 2000.

(51) Int. Cl.$^7$ .................................................. A61B 1/32
(52) U.S. Cl. .......................... 600/232; 600/231; 600/210; 600/201
(58) Field of Search ................................. 600/201, 203, 600/206, 207, 208, 210, 231, 233

(56) References Cited

U.S. PATENT DOCUMENTS

| | | | |
|---|---|---|---|
| D. 319,502 | 8/1991 | Michelson | D24/135 |
| D. 381,746 | 7/1997 | Koros et al. | D24/133 |
| D. 397,791 | 9/1998 | Koros et al. | D24/135 |
| D. 403,066 | 12/1998 | DeFonzo | D24/135 |
| D. 411,617 | 6/1999 | Furnish | D24/135 |
| D. 422,704 | 4/2000 | Segermark et al. | D24/135 |
| D. 425,200 | 5/2000 | Segermark et al. | D24/135 |
| D. 428,148 | 7/2000 | Segermark et al. | D24/135 |
| D. 428,989 | 8/2000 | Segermark et al. | D24/135 |
| 475,975 | 5/1892 | Clough . | |
| 1,157,202 | 10/1915 | Bates et al. . | |
| 2,812,758 | 11/1957 | Blumenschein . | |
| 3,016,899 | 1/1962 | Stenvall | 128/348 |
| 3,017,887 | 1/1962 | Heyer | 128/348 |
| 3,021,842 | 2/1962 | Flood | 128/215 |
| 3,364,919 * | 1/1968 | Hunnicutt . | |
| 3,656,485 | 4/1972 | Robertson | 128/349 R |
| 3,807,393 | 4/1974 | McDonald . | |
| 3,863,639 | 2/1975 | Kleaveland | 128/303 R |
| 3,893,454 | 7/1975 | Hagelin . | |
| 4,112,934 | 9/1978 | Rizk . | |
| 4,421,107 * | 12/1983 | Estes et al. . | |
| 4,492,229 | 1/1985 | Grunwald | 128/303 R |
| 4,726,356 | 2/1988 | Santilli et al. . | |
| 4,765,311 | 8/1988 | Kulik et al. . | |
| 4,971,037 | 11/1990 | Pelta . | |
| 4,998,938 | 3/1991 | Ghajar et al. | 606/130 |

(List continued on next page.)

FOREIGN PATENT DOCUMENTS

| | | | |
|---|---|---|---|
| 40 28 651 | 3/1992 | (DE) | A61B/17/02 |
| 0 792 620 A2 | 9/1997 | (EP) | A61B/17/02 |
| 0 792 620 A3 | 1/1998 | (EP) | A61B/17/02 |

(List continued on next page.)

OTHER PUBLICATIONS

Promotional literature for Cardio Thoracic Systems, published on the Internet at least as early as Feb. 1998.

*Primary Examiner*—Jeffrey A. Smith
(74) *Attorney, Agent, or Firm*—Michael S. Sherrill

(57) ABSTRACT

A tissue compression shield can help minimize trauma to tissue during surgical retraction. One such shield has a shell having a rigid outer surface adapted to abut a surgical retractor and a concave inner surface defining an elongate tissue-receiving channel. The concave inner surface is adapted to deform under localized pressure to increase surface area in contact with tissue within the channel, thereby more widely distributing pressure across the tissue. If so desired, the shield can include a compressible inner pad that contacts the tissue. In an alternative design, a shield employs a shell including a central body and a pair of opposed legs defining therebetween an elongate tissue-receiving channel. An upper one of the legs has a notch along an outer edge thereof which defines a bone-seating recess which is smaller than the tissue-receiving channel.

26 Claims, 12 Drawing Sheets

U.S. PATENT DOCUMENTS

| | | | |
|---|---|---|---|
| 5,088,472 | 2/1992 | Fakhrai . | |
| 5,125,396 | 6/1992 | Ray . | |
| 5,159,921 * | 11/1992 | Hoover . | |
| 5,201,742 | 4/1993 | Hasson | 606/130 |
| 5,375,588 | 12/1994 | Yoon . | |
| 5,391,156 | 2/1995 | Hildwein et al. | 604/174 |
| 5,425,357 | 6/1995 | Moll et al. . | |
| 5,460,170 | 10/1995 | Hammerslag | 600/201 |
| 5,505,690 | 4/1996 | Patton et al. | 600/210 |
| 5,512,038 | 4/1996 | O'Neal et al. | 600/210 |
| 5,514,076 | 5/1996 | Ley | 600/206 |
| 5,520,610 * | 5/1996 | Giglio et al. | 600/233 |
| 5,522,791 | 6/1996 | Leyva | 600/207 |
| 5,540,648 | 7/1996 | Yoon | 600/114 |
| 5,613,937 | 3/1997 | Garrison et al. | 600/201 |
| 5,616,117 | 4/1997 | Dinkler et al. | 600/232 |
| 5,658,272 | 8/1997 | Hasson | 606/1 |
| 5,688,223 | 11/1997 | Rosendahl | 600/215 |
| 5,776,054 | 7/1998 | Bobra | 600/219 |
| 5,788,630 | 8/1998 | Furnish | 600/232 |
| 5,865,731 | 2/1999 | Lexon et al. | 600/232 |
| 5,931,778 | 8/1999 | Furnish | 600/232 |
| 5,951,466 | 9/1999 | Segermark et al. | 600/225 |
| 6,231,506 * | 5/2001 | Hu et al. | 600/210 |

FOREIGN PATENT DOCUMENTS

| | | | |
|---|---|---|---|
| WO 96/02195 | 2/1996 | (WO) | A61B/17/02 |
| WO 98/12960 | 4/1998 | (WO) | A61B/1/22 |
| WO 99/52445 | 10/1999 | (WO) | A61B/17/02 |
| WO 99/52448 | 10/1999 | (WO) | A61B/17/02 |

\* cited by examiner

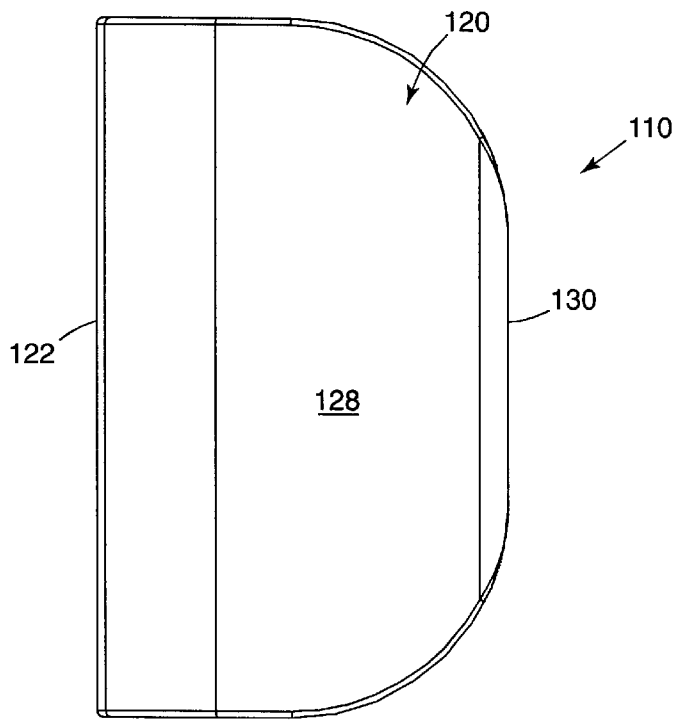
*Fig. 11*
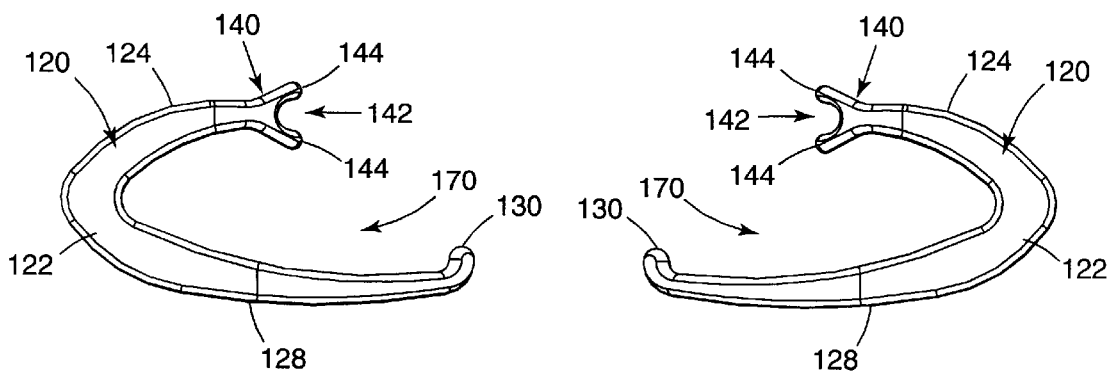
*Fig. 12*  *Fig. 13*

SOFT TISSUE COMPRESSION SHIELD AND METHOD OF RETRACTING TISSUE

This application claims the benefit of United States Provisional Application No. 60/195,229, filed Apr. 6, 2000.

FIELD OF THE INVENTION

The present invention generally provides a tool for use in holding tissue in an atraumatic fashion and has particularly utility when used in retracting tissue away from an incision or other related applications.

BACKGROUND OF THE INVENTION

Surgeons frequently need to gain access to patients' body cavities to perform various procedures. One way to gain access to such a cavity is to perform invasive surgery where the cavity is opened fairly widely from the exterior to allow the surgeon ready access to the interior of the cavity. For example, in most traditional heart surgery, the patient's sternum is split and the overlying tissue is cut back to allow the surgeon to place both hands inside the chest cavity.

Increasingly, however, less invasive techniques are being employed to permit access to body cavities. For example, endoscopic examinations are being used to explore body cavities without having to directly visually inspect them. Gall bladder surgery is also being done increasingly by gaining access to the abdominal cavity through smaller access ports through the abdominal wall rather than using more invasive approaches. (See, for example, U.S. Pat. No. 5,375,588, issued to Yoon).

Increasingly, surgeons are gaining access to the thoracic cavity by passing surgical instruments into the cavity through the intercostal spaces between a patient's ribs. For example, U.S. Pat. No. 5,613,937 (Garrison et al., the teachings of which are incorporated herein by reference) suggests a method of conducting closed-chest heart surgery by passing surgical implements through a number of ports positioned in the intercostal spaces. This patent shows one access cannula which provides an oblong opening which allows a surgeon to pass a replacement valve into the thoracic cavity for placement in the patient's heart.

A wide variety of surgical retractors are also known in the art. Most surgical retractors are intended to allow a surgeon to forcibly urge tissue out of the way to enable unfettered access to the underlying anatomical structures. Most common tissue retractors have a pair of blades which are designed to be inserted into the incision in the patient's tissue and spread laterally apart from one another to expand the incision. These blades commonly take the place of relatively flat paddles which are simply inserted into the incision. Some researchers have proposed using a somewhat curved blade in the interest of reducing trauma to the tissue. For example, O'Neill et al., U.S. Pat. No. 5,512,038, proposed a variety of curved blade designs having varying degrees of complexity. These blades are attached to a standard retraction system employed for back surgery and may be swapped out with other blades to provide the desired shape for any given procedure. In U.S. Pat. Nos. 5,788,630 and 5,931,778, Furnish suggests articulatible blades having an angled configuration. In use, each blade abuts a patient's ribs with their angled surface.

U.S. Pat. No. 4,726,356, issued to Santilli et al., shows a thoracic retractor having a pair of cuffs. Both of these cuffs have a curved contour and are said to engage the sides of the chest incision to permit access to the internal organs. Lenox et al. discloses another retractor in U.S. Pat. No. 5,865,731.

FIGS. 5–9 illustrate a retractor having repositionable blades, each of which has a pair of C-shaped grips.

Such prior art retractors tend to cause undue trauma to the tissue and increase the risk of damage to the nerves. This is particularly acute when the tissue retractors are used adjacent a hard, bony structure such as a patient's ribs. Tissue tends to get pinched between the hard blades of the retractor and the hard, bony structure. As a result, the brunt of the force applied against the tissue to widen the incision tends to be borne by a fairly localized area of the tissue. This causes significant trauma to the affected tissue and any structure included within that tissue. For example, any vessels passing through the tissue which is subjected to the increased stress can be traumatized, leading to hematomata adjacent the site. Any nerves passing through this area of the tissue can also experience long-term damage, some of which may never be fully recovered.

The use of curved retractor blades may help address this issue, but they are not believed to provide an effective solution. If the contours of the curved blades were to precisely match the contours of the bony structure with the overlying tissue, this may effectively distribute the force of the retractor blade over a larger area and help minimize A trauma to the issue. As a practical matter, though, a mass-produced retractor blade simply cannot precisely match the contour of each and every patient's body structures. Even if the blade did match the shape of the rib initially upon insertion, the rib will tend to bend somewhat and change its orientation as the ribs are spread apart from one another, leading to a poor fit between the blade and the rib. As a consequence, significant trauma to the tissue adjacent an incision is common even when surgical retractors with curved blades are used.

SUMMARY OF THE INVENTION

The present invention contemplates a tissue compression shield which may be used with a surgical retractor if so desired. The invention also contemplates a method of retracting tissue which helps minimize damage to the tissue attributable to localized concentration of forces applied to the tissue.

In a device according to one embodiment of the invention, the tissue compression shield comprises a shell which has a rigid outer surface adapted to mechanically engage a surgical retractor and has a concave inner surface defining an elongate tissue-receiving channel. The concave inner surface is adapted to deform under localized pressure to increase surface area in contact with the tissue within the channel, thereby more widely distributing pressure across the tissue. If so desired, the shell may carry a compressible inner pad, which defines at least a portion of the concave inner surface. In such an embodiment, the pad is ideally formed of a compressible polymeric material which permits the deformation of the inner surface noted above.

In a more specific embodiment, a tissue compression shield includes a rigid outer shell and a compressible inner pad. The rigid outer shell has an outer surface adapted to abut a surgical retractor and has a concave inner surface defining an elongate tissue-receiving channel. The inner pad is carried on the inner surface of the outer shell within the tissue-receiving channel. The inner pad is adapted to deform under localized pressure to increase surface area in contact with the tissue within the channel, thereby more widely distributing pressure across the tissue.

An alternative embodiment of the invention provides a tissue compression shield which is better adapted to minimize twisting or turning of the shield during use with certain types of retractors. In accordance with this embodiment, the shield includes a shell and a retractor-engaging surface. The shell has a concave inner surface defining an elongate tissue-receiving channel which has a width and is open along a first side of the shell. The concave inner surface is compressible and adapted to deform under localized pressure. The retractor-engaging surface is carried by the shell on a second side opposite the first side. The retractor-engaging surface extends laterally beyond the width of the channel on at least one side of the channel. In one particularly preferred adaptation of this embodiment, the retractor-engaging surface comprises a surface of a flange which depends downwardly from the shell's body.

In yet another alternative embodiment, the invention contemplates a tissue compression shield comprising a shell having a central body and a pair of opposed legs extending outwardly away from the central body. The central body and the opposed legs define there between an elongate tissue-receiving channel. An upper one of the legs includes a notch extending along an outer edge thereof This notch defines a bone-seating recess which is smaller than the tissue-receiving channel. If so desired, a compressible inner pad such as that noted above can be included on the inner surface of the shell within the tissue-receiving channel and/or within the bone-seating recess.

Another embodiment of the invention provides a surgical retraction system comprising a retractor and a tissue compression shield. The retractor has a pair of engagement surfaces operatively linked to one another to permit a user to selectively urge the engagement surfaces away from one another to spread an incision made in tissue. The tissue compression shield has a shell having a rigid outer surface and a concave inner surface defining an elongate tissue-receiving channel. The outer surface is in mechanical engagement with at least one of the retractor's engagement surfaces. The concave inner surface is adapted to deform under localized pressure to increase surface area in contact with tissue within the channel, thereby more widely distributing pressure across the tissue.

In a more specific embodiment, the surgical retraction system includes a retractor generally as noted above. The tissue compression shield has a rigid outer shell and a compressible inner pad. An outer surface of the outer shell is in compressive engagement with at least one of the retractor's engagement surfaces. The rigid outer shell has a concave inner surface defining an elongate tissue-receiving channel. The inner pad is carried on that inner surface within the tissue-receiving channel. The inner pad is adapted to deform under localized pressure to increase surface area and contact within the channel, thereby more widely distributing pressure across the tissue.

As noted above, the present invention also contemplates a method of retracting a patient's tissue. In accordance with this method, a tissue compression shield is provided. This tissue compression shield ideally has a shell having a rigid outer surface and a compressible, concave inner surface defining a tissue-receiving channel. The tissue compression shield is placed within an incision in the patient's tissue with tissue on one side of the incision being received with in the channel and contacting the compressible inner surface of the shield. The incision is spread by urging against the outer surface of the tissue compression shield, thereby urging the inner surface outwardly against the tissue against the channel and causing the compressible inner surface to compress such that it deforms to better conform to a surface of the tissue within the channel, thereby more widely distributing pressure across the tissue.

BRIEF DESCRIPTION OF THE DRAWINGS

FIG. 11 is a bottom view of the tissue compression shield of FIG. 9.

FIG. 12 is a left end view of the tissue compression shield of FIG. 9.

FIG. 13 is a right end view of the tissue compression shield of FIG. 9.

DETAILED DESCRIPTION OF THE PREFERRED EMBODIMENTS INCLUDING BEST MODE

Figure 1:
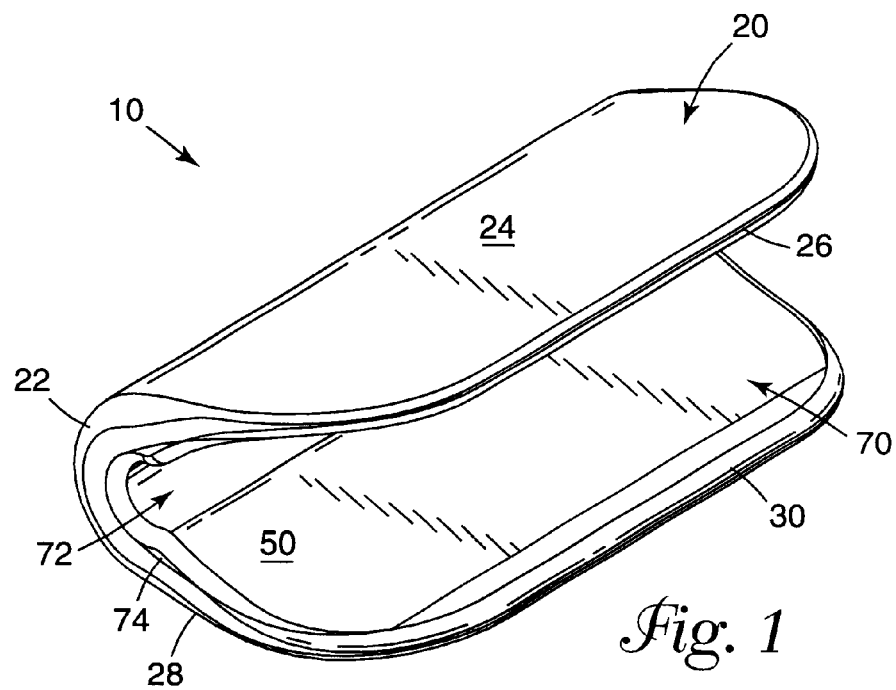
FIG. 1 is a top perspective view of a tissue compression shield in accordance with one embodiment of the invention.
Figure 2:
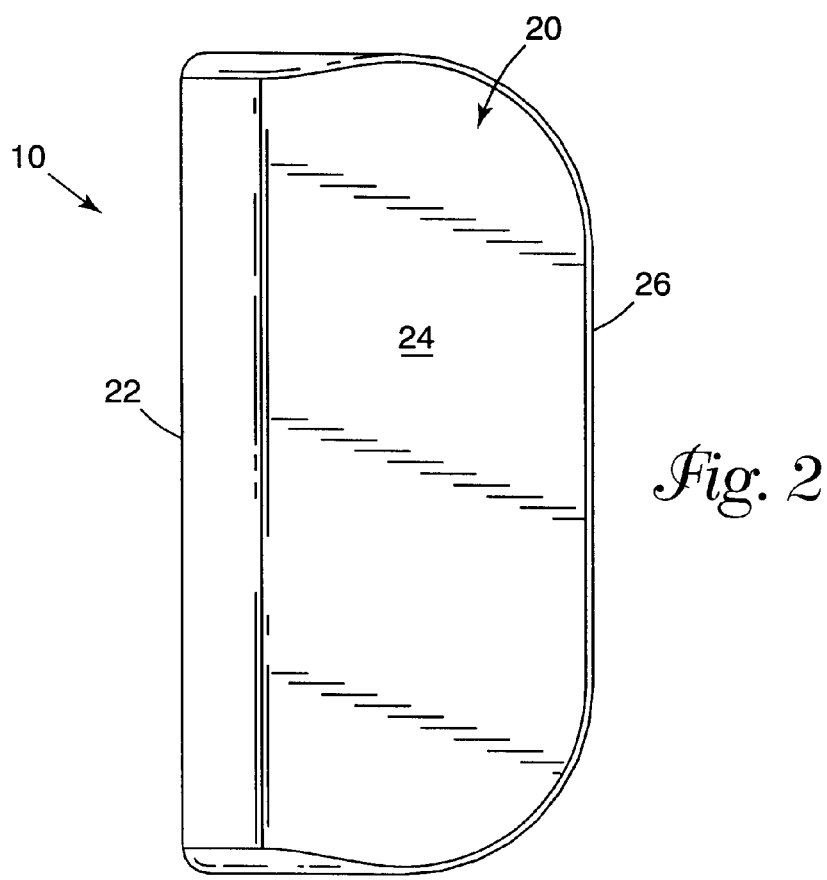
FIG. 2 is a top view of the tissue compression shield of FIG. 1.
Figure 3:
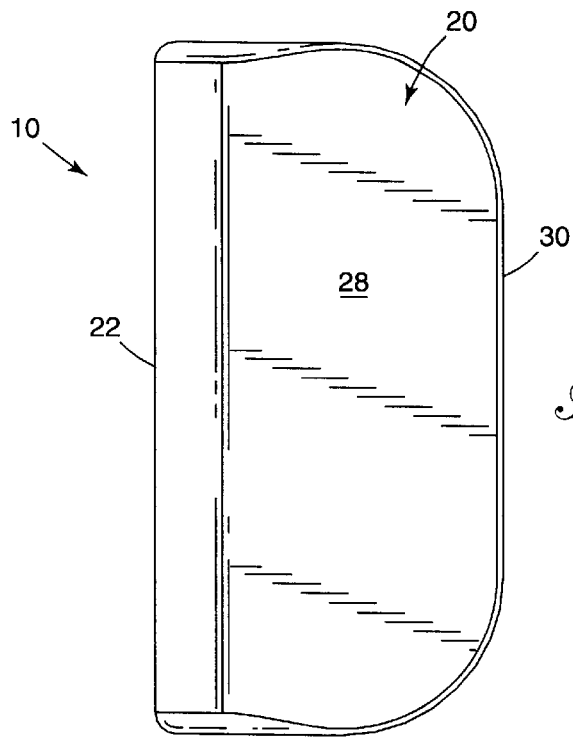
FIG. 3 is bottom view of the tissue compression shield of FIG. 1.
Figure 4:
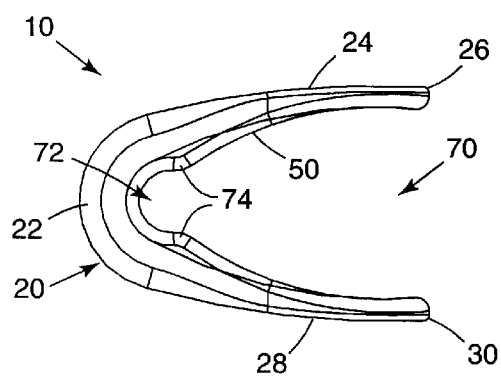
FIG. 4 is a left end view of the tissue compression shield of FIG. 1.
Figure 5:
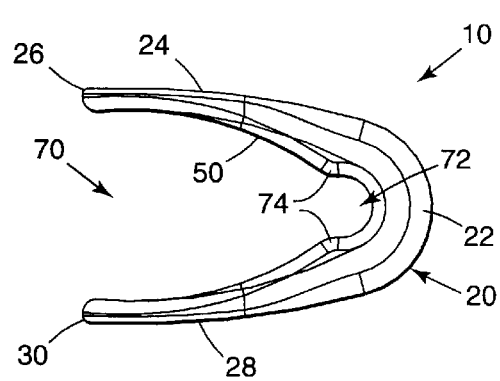
FIG. 5 is a right end view of the tissue compression shield of FIG. 1.
Figure 6:
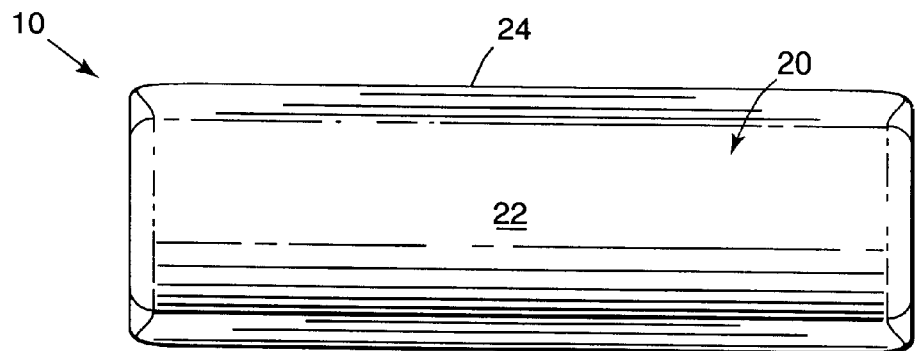
FIG. 6 is a rear view of the tissue compression shield of FIG. 1.
Figure 7:
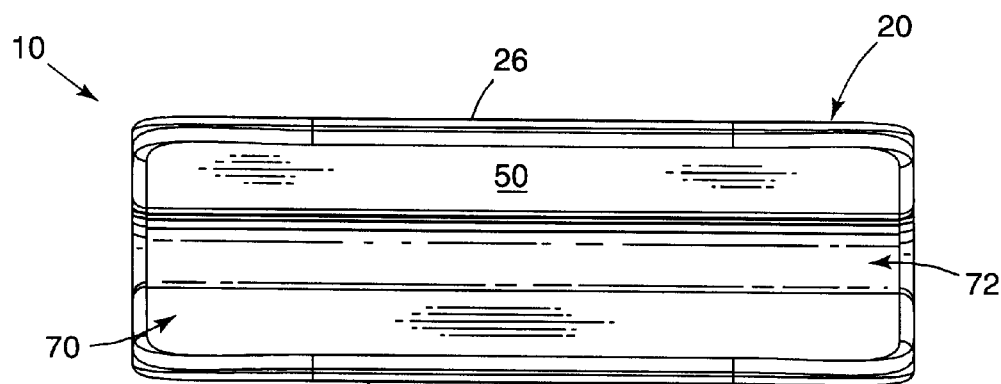
FIG. 7 is a front view of the tissue compression shield of FIG. 1.

FIGS. 1–8 schematically illustrate one of the more rudimentary embodiments of the present invention. This embodiment provides a tissue compression shield 10 generally comprising a rigid outer shell 20 and a compressible inner pad 50. The shell can take on any desired shape, but it is desirably relatively rigid, or at least provides a rigid outer surface which can abut a surgical retractor. The shell need not be completely rigid, but should be able to withstand the forces exerted by the surgical retractor in the process of retracting tissue without undue bending or other deformation. The shell 20 of FIGS. 1–8 is generally U-shaped in cross section and has a central body 22 and a pair of opposed legs 24, 28 extending away from the central body. The upper leg 24 has an outer edge 26 at the end disposed away from the central body and the lower leg 28 has an outer edge 30 at the edge spaced away from the central body.

This U-shaped shell 20 defines a tissue-receiving channel 70 extending along the length of the shield. The channel 70 is bounded on its upper side by the upper leg 24 and on its lower side by the lower leg 28. The curved central body 22 generally defines the inner extent of the U-shaped channel 70.

The shell may be formed of any suitable material. If so desired, it may be formed of stainless steel, titanium or another metal so it can be sterilized and reused, either with or without replacing the inner pad 50. It is currently contemplated, though, that the entire tissue compression shield 10 will be disposable after a single use and that the shell will be formed of a relatively rigid polymeric material which is readily molded by injection molding or the like. It is generally preferred that the material have a Young's tensile modulus of at least about $2.3 \times 10^9$ Mpa. One polymeric material which is believed to be suitable for this purpose is a USP class XI polycarbonate sold by Bayer Aktiengesellschaft (Leverkusen, Germany) under the trade name MAKROLON 2458-1112.

A compressible inner pad 50 is carried on the inner surface of the outer shell 20 within the tissue-receiving channel 70. This inner pad may generally track the shape of the inner surface of the rigid outer shell. Optimally, this inner pad 50 defines a majority of the inner surface of the tissue compression shield 10 and helps define the tissue-receiving channel of the device. As best seen in the cross-sectional view of FIG. 8, the inner pad 50 need not have a constant thickness across the entire inner surface of the outer shell 20. Instead, the thickness of the pad may be varied to define a different shape for the tissue-receiving channel 70 and to provide additional padding at certain locations than at other locations.

In the illustrated embodiment, the inner pad 50 is thinnest along the inner surface of the legs 24, 28 adjacent the outer edges (26, 30, respectively) thereof. The thickest areas of the pad are positioned toward the middle of the channel 70, generally adjacent the junction between the legs and the central body 22. In the embodiment of FIGS. 1–8, the inner pad 50 has a reduced thickness along the interior surface of the central body 22, defining an inner relief channel 72, and the thickest areas of the pad define soft shoulders 74 which are adapted to engage a structure within the tissue being retracted, such as a rib or other bony structure. The relief channel is optimally sized to receive a significant volume (ideally, a majority) of the tissue overlying the rib or other structure, permitting much of the retracting force to be transferred to the bone via the shoulders 74 while the nerves, blood vessels and the like within the softer overlying tissue is protected from undue harm by resting in the relief channel 72.

The inner pad 50 is formed of a relatively soft, compressible material which is adapted to deform under localized pressure when the shield is used to retract a patient's tissue. At a minimum, the inner pad 50 should be formed of a material having a hardness less than the hardness of the material of which the outer shell 20 is formed. Preferably, the inner pad is formed of a polymeric material which is substantially softer than the relatively rigid shell. While the precise characteristics of the inner pad can be changed to meet specific design objectives for different applications, an inner pad having a hardness of no more than 30 Shore A, and more desirably ranging from 20–30 Shore A, is believed to work well. As it is contemplated that the tissue compression shield 10 is likely to be disposed after a single use, the enhanced compressibility of such a relatively soft materials is preferred despite the likely reduction in toughness which could result in the reduction of the useful life of the inner pad if it were intended for multiple reuse.

If the inner pad is formed by overmolding it atop the shell 20, as discussed below, a material which will form a reasonably strong bond with the shell should be selected. For example, if the shell is formed of a polycarbonate material (e.g., Bayer's MARKOLON 248-1112 noted above), it is believed that many soft urethane compounds would form a strong enough chemical bond. One urethane commonly used in overmolding atop polycarbonates is sold by The Dow Chemical Company (Midland, Mich., USA) under the tradename PELLETHANE.

Figure 8:
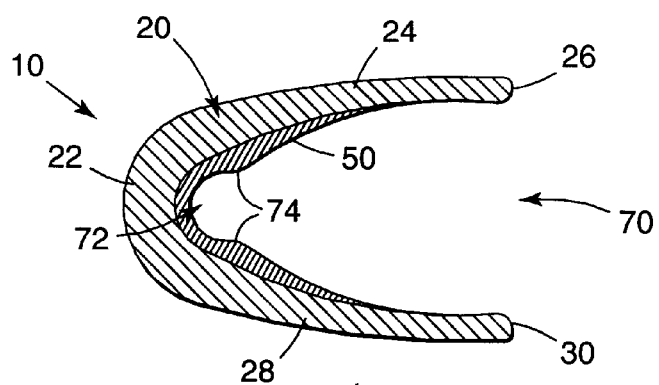
FIG. 8 is a schematic cross-sectional view taken along line 8—8 of FIG. 2.
Figure 9:
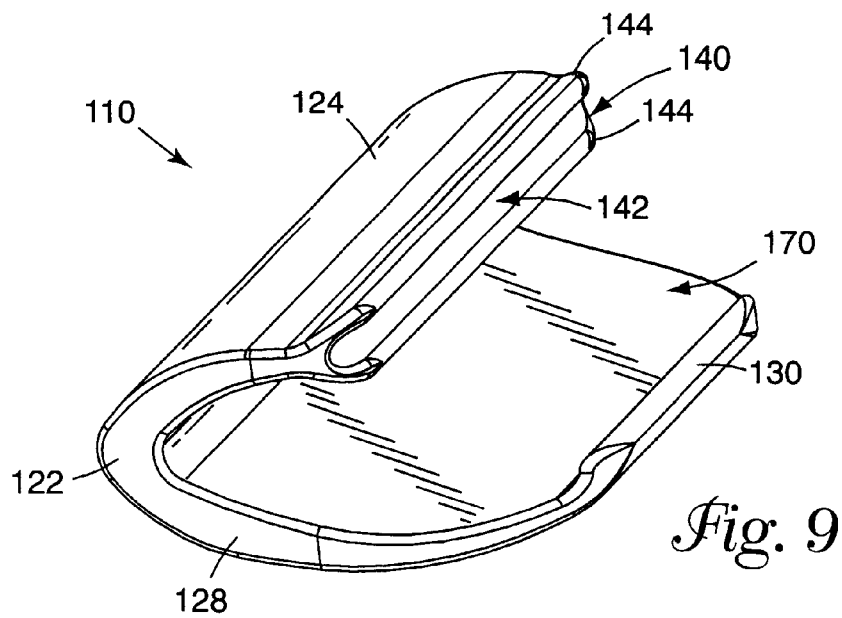
FIG. 9 is a perspective view of a tissue compression shield in accordance with an alternative embodiment of the invention.
Figure 10:
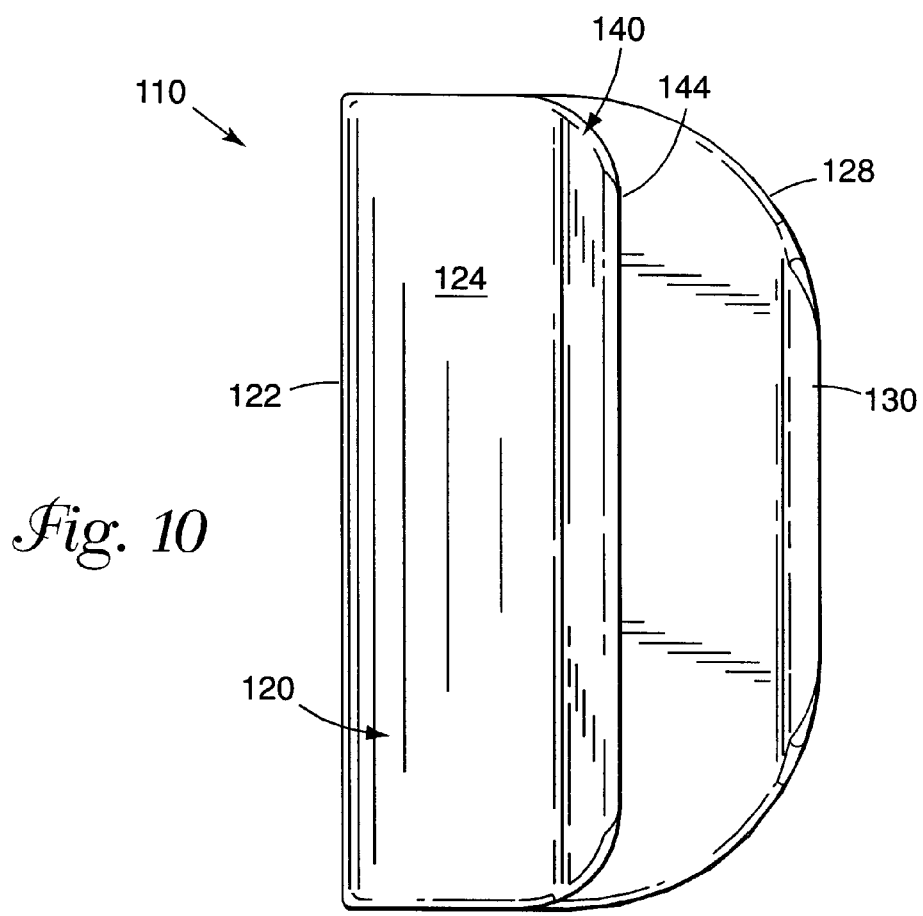
FIG. 10 is a top view of the tissue compression shield of FIG. 9.
Figure 14:
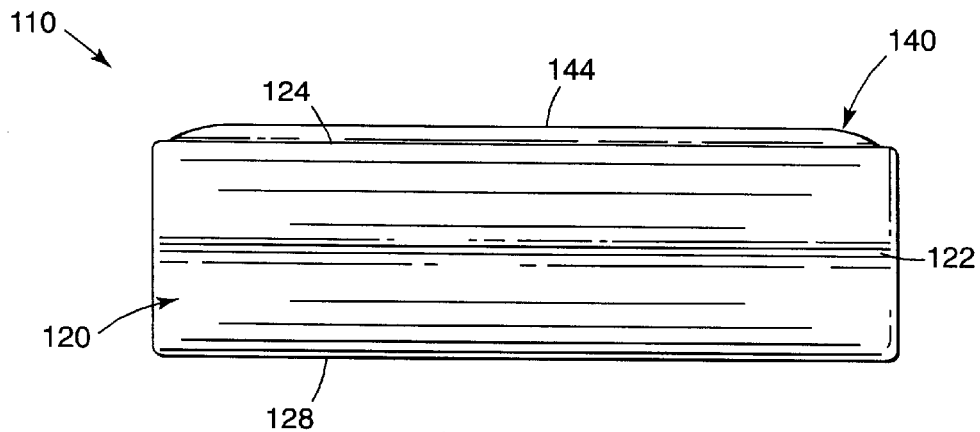
FIG. 14 is a rear view of the tissue compression shield of FIG. 9.
Figure 15:
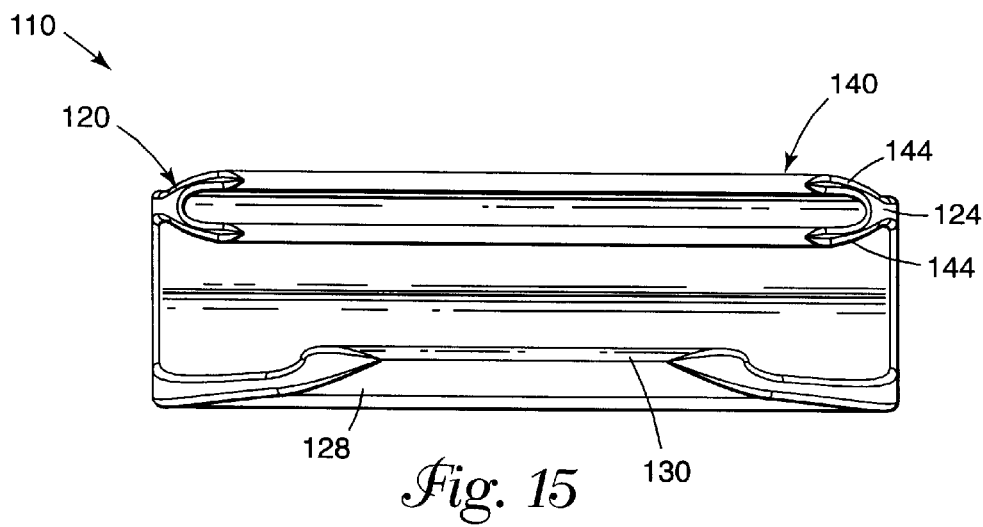
FIG. 15 is a front view of the tissue compression shield of FIG. 9.

Ideally, the central body 22 and the legs 24, 28 of the shell 20 are all integrally formed of the same material in a single molding operation. As best seen in FIG. 8, the thickness of the central body 22 is greater than the thickness of either the upper leg or the lower leg 28 adjacent their respective outer edges 26, 30. This permits the shell to have its greatest strength and rigidity in the area where it will come into direct contact with the blades of the retractor, i.e., in its central body 22. In addition, tapering the thickness of the legs in a direction moving away from the central body and toward their respective outer edges will afford some degree of flexibility of the legs 24, 28. While these legs should remain relatively rigid, a small degree of flexural ability can be advantageous when the physician is placing the tissue compression shield 10 into the incision to surround the tissue adjacent the incision.

The inner pad 50 can be connected to the shell 20 in any desirable fashion. For example, the inner pad 50 can be formed separately, e.g., in a separate molding operation, and attached to the inner surface of the shell 20 by means of a suitable adhesive or mechanical linkage. It is generally preferred, though, to add the inner pad 50 to the tissue compression shield in an overmolding operation. In such a procedure, which is known in the field of plastics molding, the pre-formed shell 20 would be introduced to a second mold. The inner pad 50 may then be injected into the mold to fill the space between the mold and the shell. If such an overmolding operation is employed, it is desirable to effectively envelop the outer edges 26 and 30 of the legs 24, 28 and the left and right sides of the shell within the material of the inner pad. This will help keep the inner pad in place on the shell without requiring additional adhesive or mechanical linkages. It should be understood, though, that this will not be strictly necessary. As a matter of fact, in the embodiment shown in FIGS. 1–8, the inner pad 50 extends along the majority of the length of the tissue-receiving channel, but tapers to approximately zero thickness adjacent the outer edge of at least one, and likely both, of the legs 24, 28. Instead of extending right up to the outer edge as shown, the inner pad instead may be spaced inwardly of the outer edge a predetermined distance.

In use, the inner pad 50 is in direct contact with the tissue and provides. a compressive layer between the rigidity of the outer shell 20 and the tissue. As will be explained more fully below in connection with FIG. 23, the inner pad 50 will tend to deform under localized pressure when the shield is urged against the tissue within the channel. This deformation increases the surface area of the shield 10 in contact with tissue, thereby more widely distributing pressure across the tissue. As a result, hematomas, nerve damage and other trauma to the tissue and underlying structures can be significantly reduced.

FIGS. 9–16 illustrate an alternative tissue compression shield 110 in accordance with a different embodiment of the invention. Many of the elements of this tissue compression shield 110 are functionally analogous to similar structures in the embodiment of FIGS. 1–8 and bear like reference numbers, but incremented by 100. For example, the tissue compression shield 110 includes a shell 120 which is analogous to the shell 20 of the tissue compression shield 10 of FIGS. 1–8.

Generally, the tissue compression shield 110 also a generally U-shaped shell 120 with a central body 122 and a pair of legs 124, 128. An inner pad may carried within the tissue-receiving channel 170. This compressible pad may be formed of the same types of materials noted above for the pad 50 in the previous embodiment and will serve much the same function. In the illustrated embodiment, though, the inner pad is omitted. It is currently believed that such a pad would not be necessary to avoid nerve damage because the majority of the forces of retraction will be borne by the notch 140 and the outer edge 130 of the lower leg 128 (as discussed below in connection with FIG. 16) and the nerves adjacent the rib will rest in the relatively safe confines of the channel 170 without being subjected to much force.

In the prior embodiment, the upper leg 24 and the lower leg 28 have about the same length and shape. Consequently, the device is generally symmetrical about a plane bisecting the tissue-receiving channel 70 and passing through the central body 22 of the shell. In the shield 110 of this embodiment, though, the upper leg 124 has a substantially different shape than the lower leg 128. The lower leg 128 is substantially wider than the upper leg 124, i.e., the outer edge 130 of the lower leg 128 is spaced farther away from the central body 122 than is the outer edge of the upper leg 124. As will be described in more detail in connection with FIG. 16 below, this permits the outer edge 130 of the lower leg 128 to urge against a different portion of a hard, bony structure (e.g., a patient's rib) than does the upper leg 124. This also provides a larger, deeper recess 170 to permit the tissue compression shield 110 to receive more of the soft tissue surrounding the bony structure than would be provided if the lower leg 28 were as short as the upper leg.

The upper leg 124 of the shield 110 also has a particularly useful feature which is not included in the shell 20 of the tissue compression shield 10 of FIGS. 1–8. More specifically, the plain, rounded outer edge 26 of the shield 10 is replaced with a notch 140 which extends along the outer edge of the upper leg. This notch defines a bone-seating recess 142 between a pair of opposed fingers 144. These fingers are desirably integrally formed with the rest of the shell 120 in a single molding operation.

As is readily apparent from the drawings, it is preferred that the notch 140 be substantially smaller than the tissue-receiving channel 170. While the length of the notch will depend on the configuration of the upper leg 124, it desirably extends along the entire outer edge of the leg 124 and, consequently, may be of about the same length as the tissue-receiving channel 170 (though this can be varied). The notch 140, however, is anticipated to be substantially more shallow than the channel 170, i.e., the fingers 144 defining the bone-seating recess 142 are substantially shorter than either the upper leg 124 or the lower leg 128.

The tissue compression shield 110 of FIGS. 9–15 has a notch which extends along the entire width of the upper leg's outer edge. It should be understood, though, that more than one notch can be used. It is contemplated that a series of aligned notches could be used, spaced apart from one another along the outer edge of the upper leg 124. his should still allow the outer edge of the upper leg 124 to seat against a rib or other bony structure, as discussed below, while permitting greater design flexibility.

Figure 16:
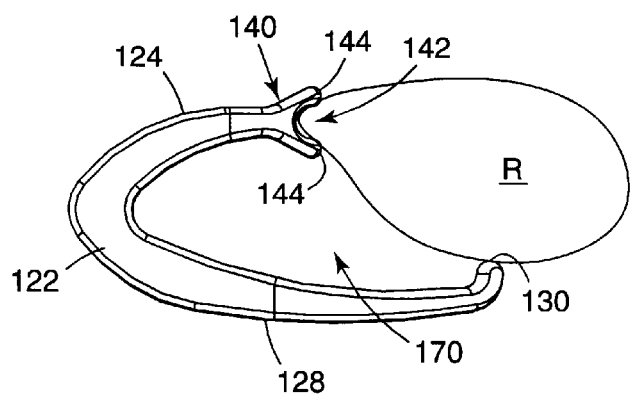
FIG. 16 is a schematic cross-sectional side view of the tissue compression shield of FIG. 9 engaging a patient's rib.
Figure 17:
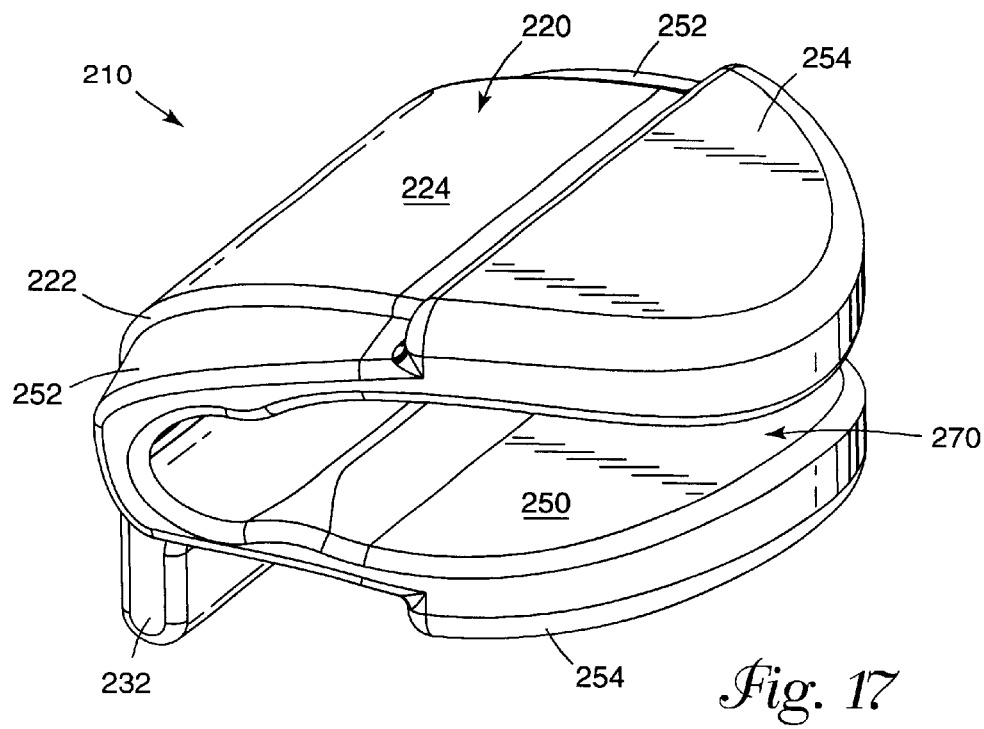
FIG. 17 is a top perspective view of a tissue compression shield in accordance with yet another embodiment of the invention.
Figure 18:
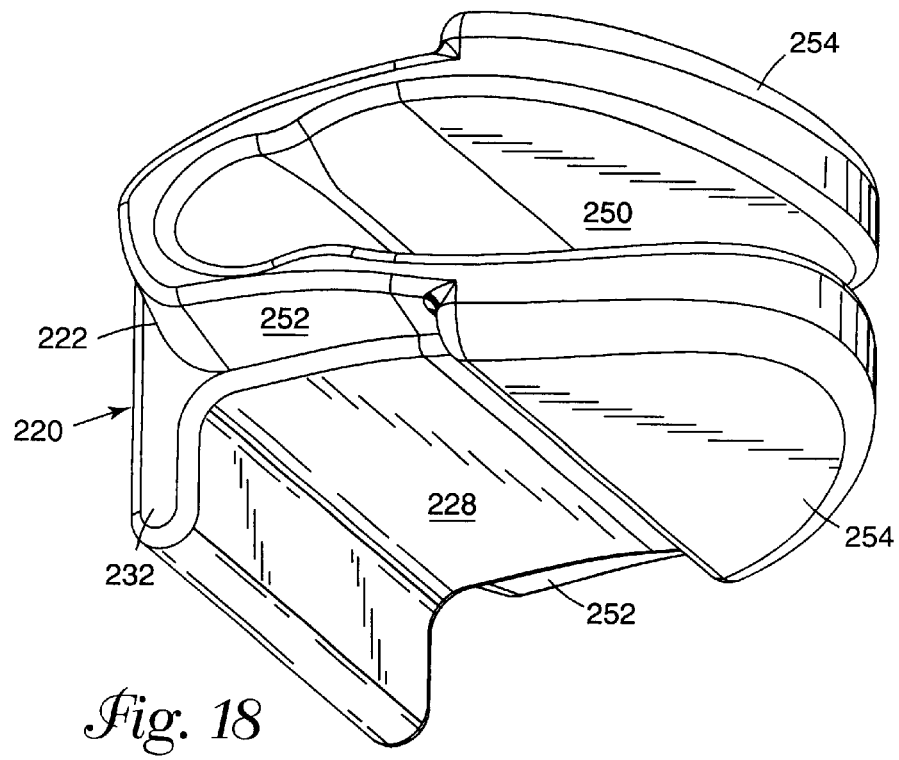
FIG. 18 is bottom perspective view of the tissue compression shield of FIG. 17.
Figure 19:
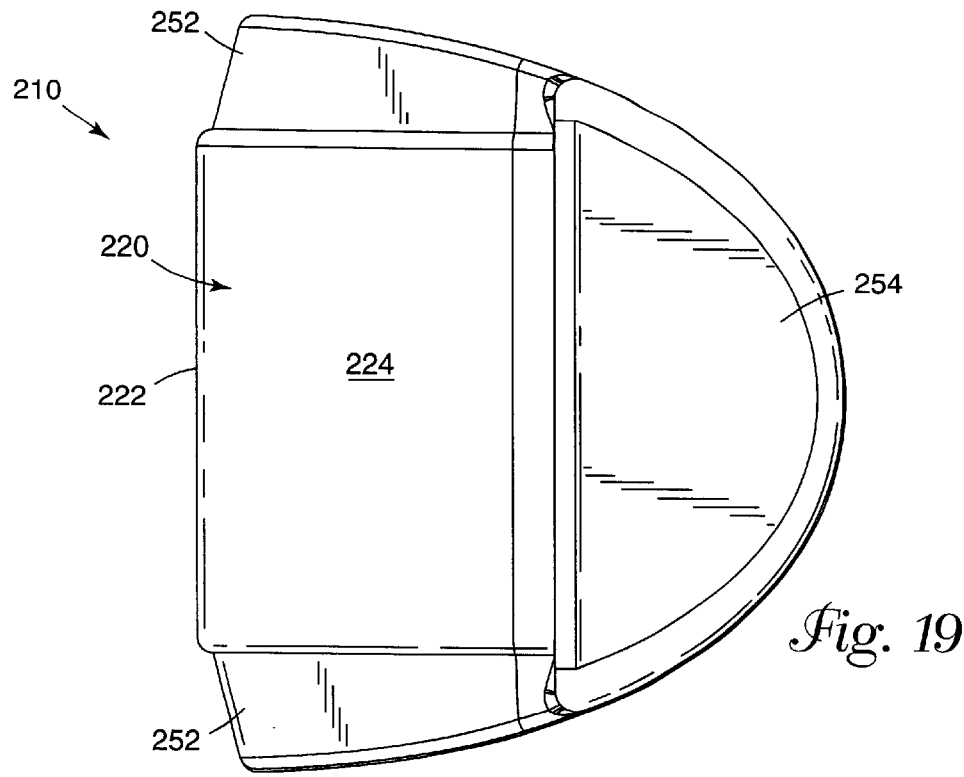
FIG. 19 is top view of the tissue compression shield of FIG. 17.
Figure 20:
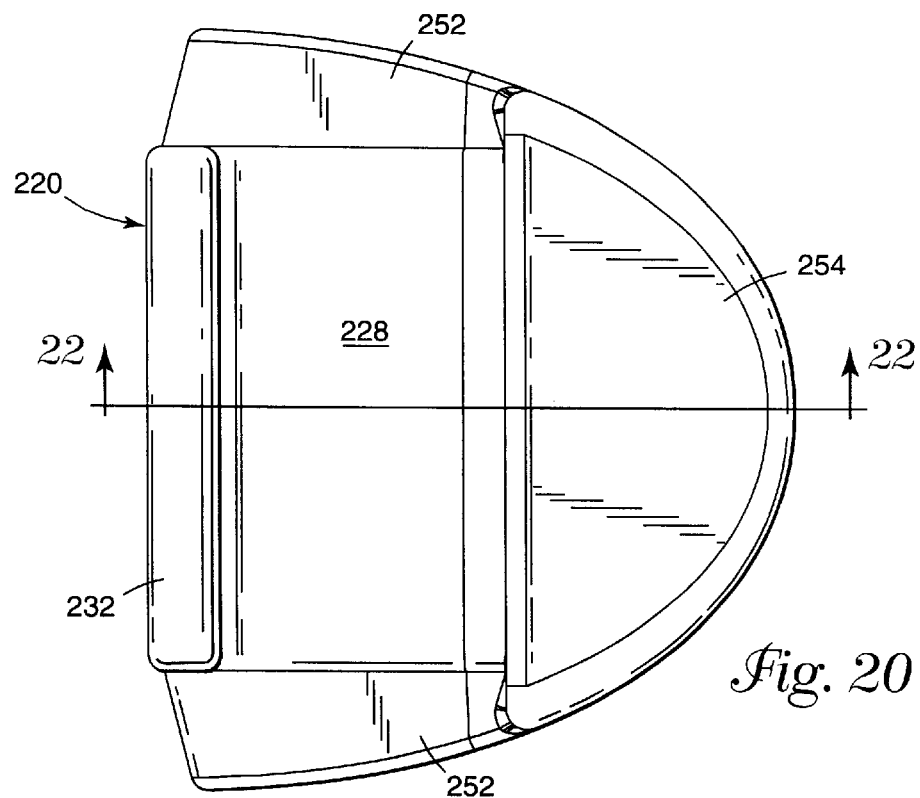
FIG. 20 is a bottom view of the tissue compression shield of FIG. 17.

FIG. 16 shows the tissue compression shield 110 of FIGS. 9–15 in use. In particular, the shield 110 has been inserted into the intercostal space between two adjacent ribs. For purposes of illustration, only one rib R is shown in FIG. 16.

The rib R has an elongated edge which is received generally within the bone-seating recess 142 of the notch 140 in the shield's upper leg 124. In most circumstances, there will be a thin layer of tissue which overlies this bone, i.e., the surgeon will not strip the tissue away from the edge of the rib R. As a consequence, the rib R itself may not come into direct contact with the notch 140. However, the tissue at this location tends to be relatively free of nerves or blood vessels, minimizing the long-term damage to the tissue due to somewhat more concentrated or localized pressure along the leading edge of the rib R.

The outer edge 130 of the lower leg 128 of the shield urges against the patient's body at a different location. In the illustrated embodiment, the lower leg 128 is not much longer than the expected width of the rib R. As a consequence, the outer edge 130 of the lower leg abuts against the tissue on the underside of the rib R. Typically, additional tissue such as fat and muscle, which includes more vasculature and nerve endings, will surround the rib and be positioned between the rib and this edge 130. This tissue has been omitted from FIG. 16 for simplicity of illustration, though. The majority of this tissue surrounding the rib will be received within the tissue-receiving channel 170 and may be compressed within that channel as explained below.

When the physician wishes to expand the intercostal incision, he may urge outwardly against the tissue compression shield 110. In the view of FIG. 16, this would comprise urging to the right against the rigid outer surface of the central body 122 This central body 122 (or at least the portion thereof which will contact a relatively flat retractor blade) is positioned below and to the left of the notch 140. Since the notch is seated against an edge of the rib R, this will induce a rotational moment in the shield, tending to pivot the shield generally counterclockwise in the view of FIG. 16 and urge the outer edge 130 of the lower leg 128 upwardly toward the rib R. This relieves pressure on the tissue within the tissue-receiving channel 170. To the extent that there is sufficient tissue overlying the rib R to completely fill that channel 170, the force of the retractor (not shown) against the shield 110 will be distributed more evenly across that tissue, minimizing damage which may result due to more localized concentration of that force.

This is in contrast to current standard procedure, wherein a flat-bladed retractor is inserted into the incision and the parallel blades are simply moved away from one another. In such a circumstance, the vast majority of the force is borne by the tissue positioned directly between the retractor and the rib R. As noted previously, this has been known to cause undue trauma to that tissue.

FIGS. 17–22 illustrate a different tissue compression shield 210 in accordance with another embodiment of that invention. Many of the elements of this tissue compression shield 210 are roughly analogous to similar structures in the embodiments of FIGS. 1–8 and bear like reference numbers, but incremented by 200. For example, the tissue compression shield 210 includes a shell 220 which is analogous to the shell 20 of the tissue compression shield 10 of FIGS. 1–8.

The shell 220 of the tissue compression shield 210 is generally U-shaped with a central body 222 and a pair of spaced-apart legs 224, 228. An inner pad 250 is carried in the tissue-receiving channel 270. To this extent, the structure is fairly similar to that shown in FIGS. 1–8 and 9–16.

One of the primary differences between the tissue compression shield of this embodiment and either of the previous embodiments is the inclusion of a flange 232 which extends downwardly from the central body 222 of the shell 220. In this embodiment, the flange is relatively flat on both sides and is generally perpendicular to the lower leg 228 of the shell. If so desired, though, the flange may have a more complex shape and merge more gradually into the lower leg 228.

Figure 21A:
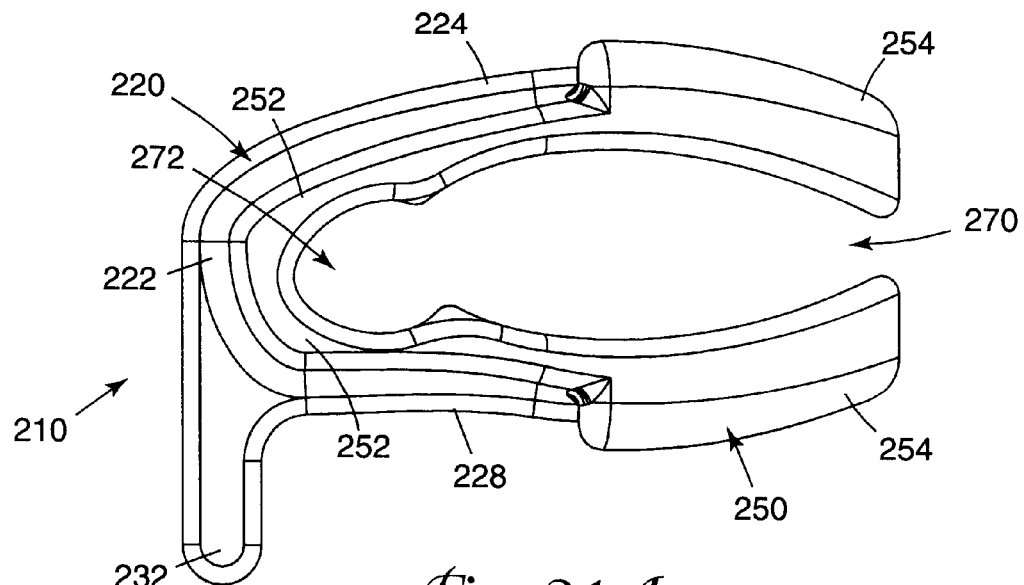
FIG. 21A is a left side view of the tissue compression shield of FIG. 17.
Figure 21B:
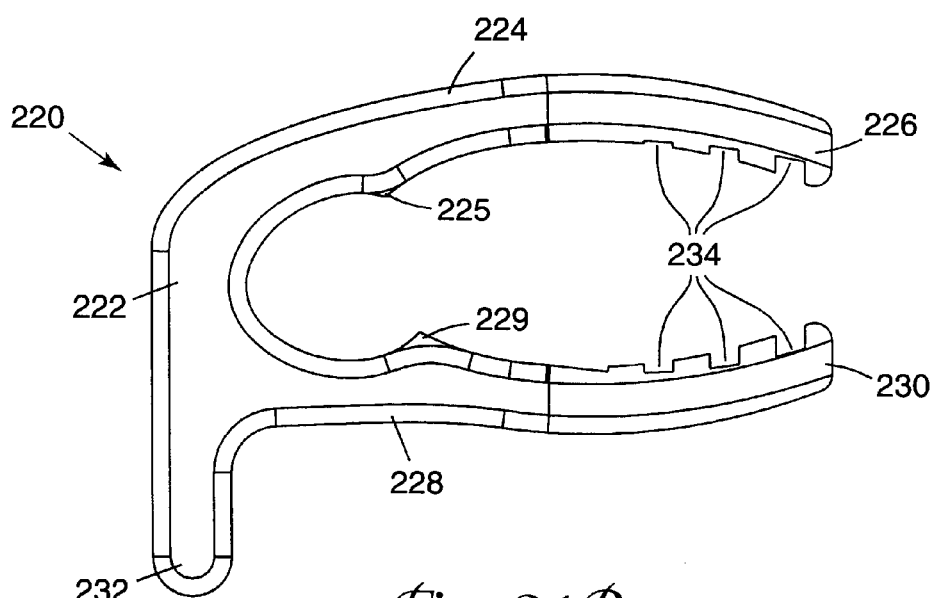
FIG. 21B is a left side view of the tissue compression shield of FIG. 17, similar to FIG. 21A, but with the inner pad removed to better illustrate the underlying structure.
Figure 22:
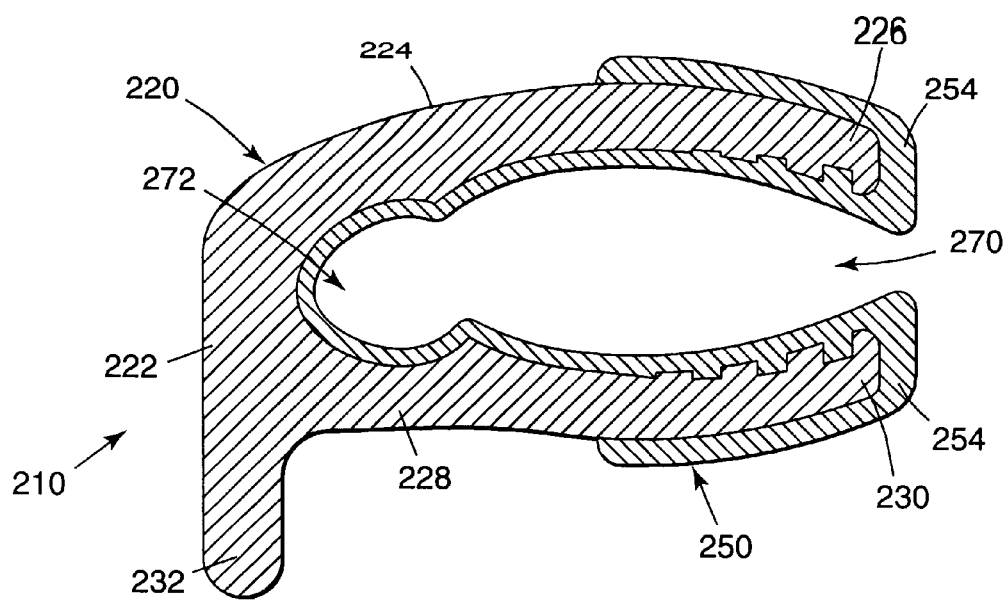
FIG. 22 is a schematic cross-sectional view taken along line 22—22 of FIG. 20.
Figure 23:
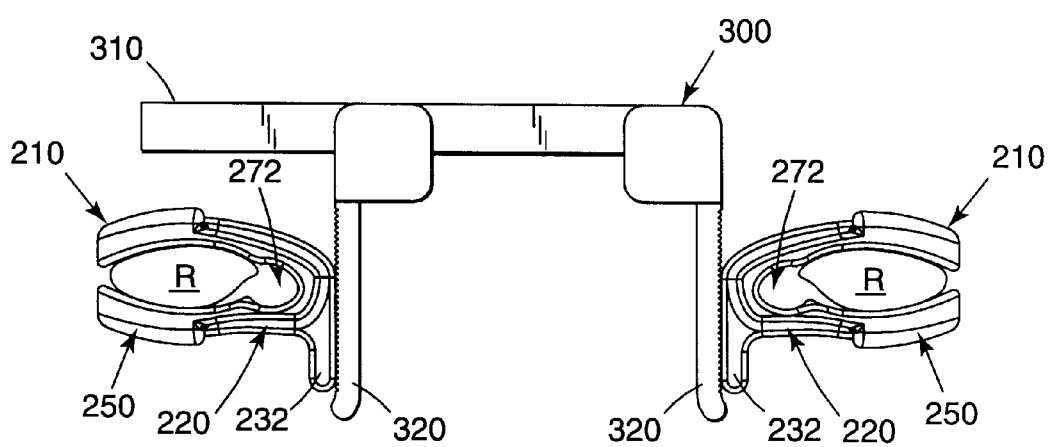
FIG. 23 is a schematic illustration of a surgical retraction system in accordance with the invention utilizing a pair of tissue compression shields similar to the shield shown in FIGS. 17–22.

Ideally, the flange has a generally flat outer surface which generally coincides with and merges tangentially into the outer surface of the central body 222 of the shell (this is best seen in FIGS. 21–23). This provides a generally flat surface which extends laterally beyond the width or depth of the tissue-receiving channel 270 on the lower side of the channel. If so desired, a second flange (not shown) can extend upwardly above the central body 222, providing a longer retractor-engaging surface for moving the retractor-engaging surface upwardly with respect to the position shown in the drawings.

In FIGS. 1–8, the tissue compression shield 10 has a central body 22 with a curved outer surface. If this is used with a relatively flat retractor blade or a retractor blade which has a significantly larger radius of curvature than the central body 22, there will be contact between the retractor blade and the shell 20 generally along a single line. There is a risk that such line contact could permit the tissue compression shield to shift under load when used to retract the tissue. While this seems unlikely to have any dangerous consequences, it is not optimal.

The tissue compression shield of FIGS. 17–22, though, tends to minimize such unplanned shifting. The retractor-engaging surface provided by the central body 222 and the flange 232 provides a substantially larger surface area of the shield 210 in contact with the retractor blade. This helps maintain the shield 210 in a consistent orientation with respect to the retractor blade. The flange 232 has a flat outer surface and is intended to be used with a relatively flat retractor blade. If the shield 210 were to be used with a retractor having a curved blade, the shape of the flange's outer surface could be adjusted accordingly to maintain good surface contact between the rigid outer surface of the shell 220 and the retractor blade.

One further advantage of the use of the downwardly depending flange 232 in the embodiment of FIGS. 17–22 is not tied solely to the increased surface area in contact with the retractor blade. Instead, this flange provides a significant surface area which extends laterally beyond the width of the tissue-receiving channel 270. In particular, this flange extends downwardly below the channel 270. When the retractor urges against the shield, the tissue may tend to try to rotate the outer edge of the shell 220 downwardly (i.e., generally clockwise in FIG. 21A). Extending the flange 232 downwardly on the opposite side of the shield will provide sufficient leverage to resist this tuning force in most circumstances.

As noted above, it is preferred that the central body 22 of the shield 10 shown in FIGS. 1–8 be stronger than and more rigid than at least one of the legs 24, 28. It was also noted that the thickness of the legs may taper away from the central body to provide increased flexibility adjacent the outer edges of the legs.

FIGS. 21–22 illustrate how this may be accomplished in the tissue compression shield 210 of FIGS. 17–22. FIG. 21B is a left side view of the shell 220 shown in FIG. 21A, but without the compressible inner pad 250 carried thereby. FIG. 22 shows the shield 210 schematically in cross section, taken along line 22—22 in FIG. 20.

In this embodiment, the upper leg 224 and the lower leg 228 each include a series of grooves 234 adjacent their respective outer edges (226 and 230 respectively). These grooves reduce the thickness of the material comprising the legs moving outwardly toward the outer edges. In the preferred embodiment shown in the drawings, these grooves vary in thickness with the thickest groove being positioned closer to the outer edge and each of the adjacent parallel grooves getting more shallow moving inwardly toward the central body 222. This will further profile the thickness to enhance flexibility more adjacent the outer edges of the legs. As will be noted below, the compressible inner pad 250 of this embodiment desirably is overmolded around a portion of the shell 220. These grooves 234 will further enhance the bond between the legs 224, 228 and the pad 250.

In the embodiment of FIGS. 17–22, the compressible inner pad 250 extends substantially beyond the periphery of the shell 220. Adjacent the back end of the tissue-receiving channel 270, the pad 250 flares outwardly from the sides of the central body 222, the upper leg 224 and the lower leg 228. This defines a pair of side wings 252 on the pad 250. Additionally, the pad 250 includes two padded tips 254, each of which extends over and preferably completely encloses the outer edge of one of the legs 224, 228. (This is best seen the cross sectional view of FIG. 22.) This provides the shield 210 with a relatively soft, atraumatic series of surfaces which come into contact with the patient's tissue. While the retractor-engaging surface of the central body 222 and flange 232 of the shell can be maintained fairly hard and rigid, all of the surfaces which come into contact with the patient's tissue are somewhat more gently rounded and are padded with the compressible pad 250. This will help minimize any damage to the tissue adjacent the edges of the device. Having a tip 254 of the pad 250 extend inwardly over the outer surface of the legs 224 and 228 from the outer edges thereof (226 and 230, respectively) helps encapsulate the distal ends of the legs. This encapsulation can be done in an overmolding process, as briefly noted above. This structure is believed to provide a strong mechanical link between the pad 250 and the shell 220. If so desired, the portion of the upper leg 224 and lower leg 228 received within a tip 254 of the pad 250 can flare outwardly beyond the width of the rest of the leg 224 or 228. This will provide a rearwardly-facing shoulder enclosed within the tip 254, further enhancing the mechanical link between the shell 220 and the pad 250.

In the embodiment of FIGS. 1–8, the thickest areas of the pad 50 define soft shoulders 74 which are adapted to engage a structure within the tissue being retracted, such as a rib R or other bony structure. The embodiment shown in FIG. 21A also includes a pad 250 with soft shoulders 274. FIG. 21B shows a pair of shoulders 225 and 229 extending from the shell 220 which correspond with the soft shoulders 274 defined by the pad 250.

FIG. 23 illustrates a pair of tissue compression shields 210 in use to spread an incision in the intercostal regions between two adjacent ribs R, R. In employing the devices in this fashion, a physician will form an incision through the tissue between the ribs. The lower leg 228 of each shield is passed through the incision and placed beneath the associated rib R. As shown in FIG. 23, this permits each of the ribs to be received within the tissue-receiving channel of the device, with the more sensitive tissue overlying the ribs being received within the inner relief channel 272.

Once the tissue compression shields are in place, the blades 320 of the retractor 300 may be positioned between the two shields. Each of the blades 320 has an engagement surface adapted to abut against the retractor-engaging surface of a tissue compression shield. These two blades 320 are operatively connected to one another to permit them to be urged away from one another. This is shown by a bar 310, which may include a ratchet mechanism to permit a physician to gain mechanical advantage in spreading the blades apart and keep them in place during an operation. Surgical retractors of this general description are well known in the art and any of a wide variety of commercially available retractors can be used in connection with the present invention.

As the retractor blades 320 urge outwardly against the retractor-engaging surfaces of the tissue compression shields 210, the shields will urge outwardly against the tissue received in their tissue-receiving channels. The compressible inner pad 250 of each of the shields will deform under localized pressure, i.e., if the inner pad is pressing harder against one part of the tissue than against another, the pad will tend to give in the areas where it is being pressed the hardest. This causes the inner pad to better conform to the surface of the tissue received within the channel, both by deforming the pad 250 and by deforming the softer portions of the tissue itself.

As a consequence of this deformation, the surface area of the pad in Contact with the tissue within the channel will increase. By distributing the retraction force of the blades 320 against a greater surface area of the tissue, the resultant pressure can be more widely distributed, helping avoid unduly high pressure at any given point in the tissue. This is believed to significantly reduce the trauma to the tissue during surgical retraction.

Figure 24:
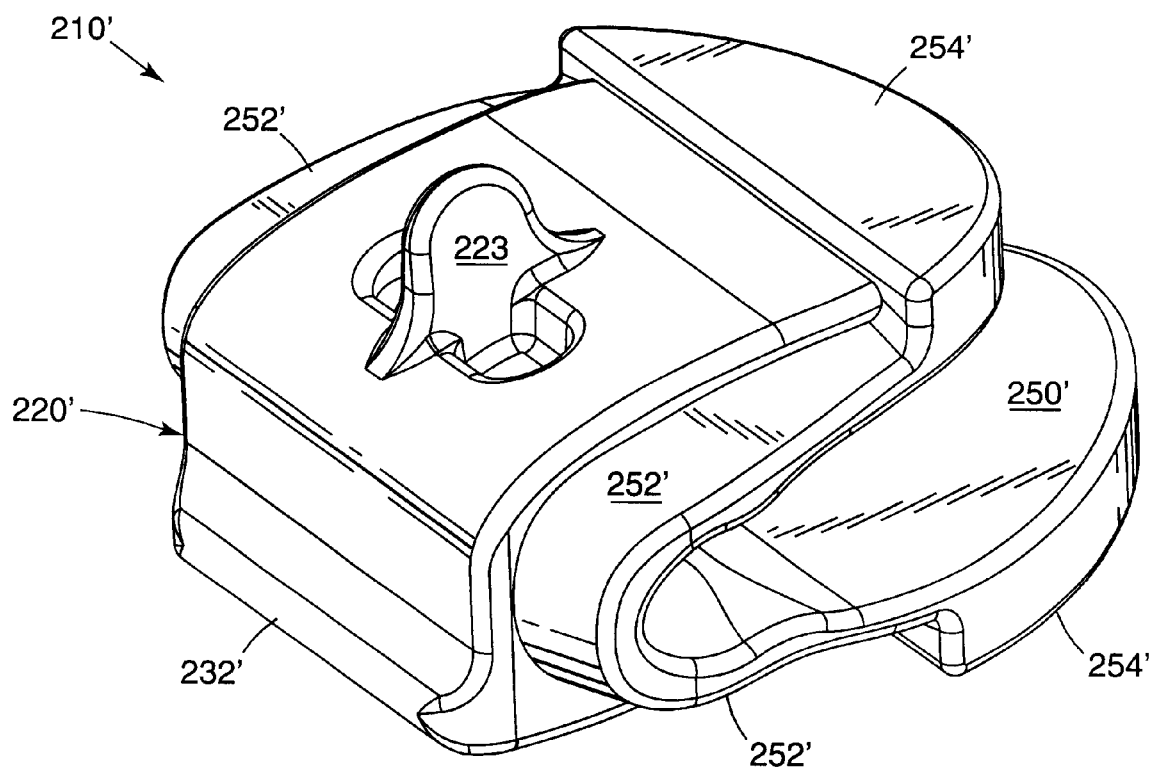
FIG. 24 is a perspective view of a tissue compression shield in accordance with still another embodiment of the invention.
Figure 25:
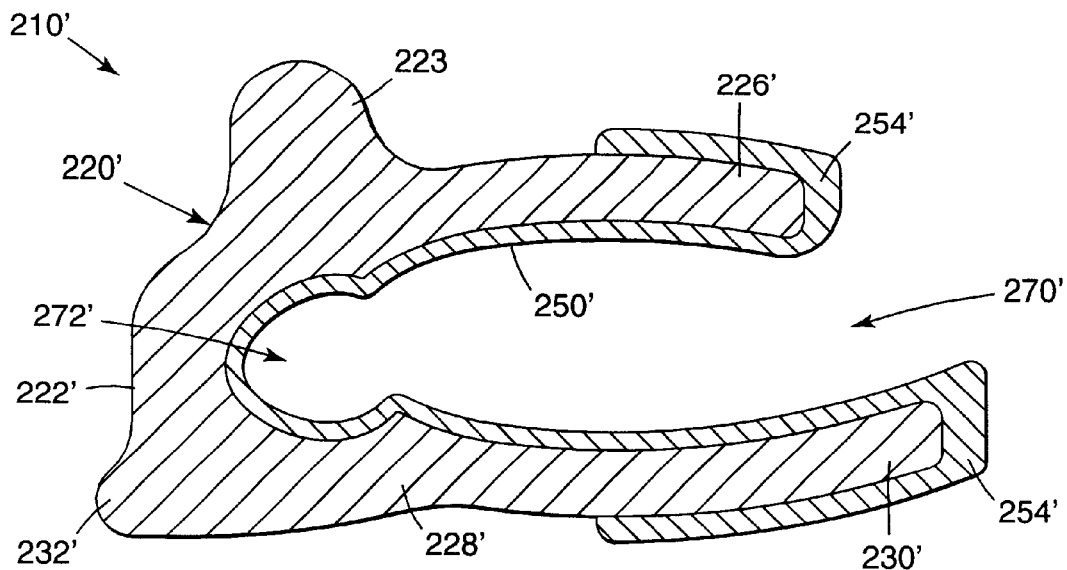
FIG. 25 is a schematic cross-sectional view taken along line 25—25 of FIG. 26.
Figure 26:
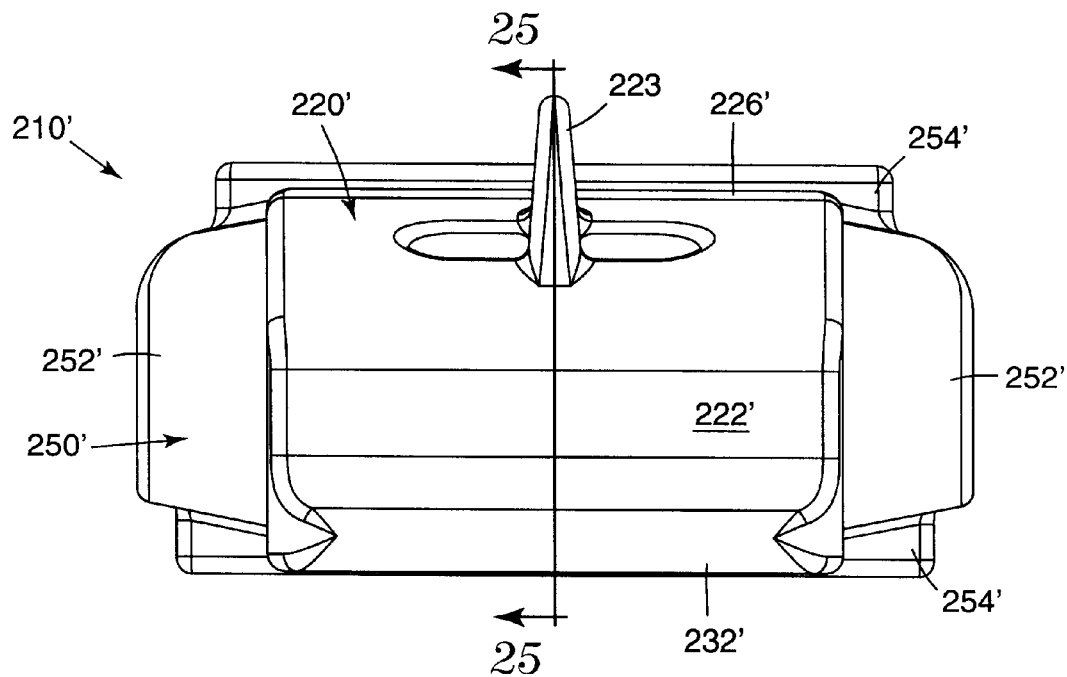
FIG. 26 is a rear view of the tissue compression shield of FIG. 24.

FIGS. 24–26 illustrate a different tissue compression shield 210' in accordance with yet another embodiment of the invention. This tissue compression shield 210' is fairly similar in many respects to the shield 210 shown in FIGS. 17–22 and like structures bear like reference numbers, but designated with a prime. For example, the tissue compression shield 210' includes a shell 220' which is analogous to the shell 220 of the tissue compression shield 210 of FIGS. 17–22.

There are two key differences between the shield 210' of FIGS. 24–26 and the prior embodiment of FIGS. 17–22— the shape of the flange 232' and the presence of a manually graspable handle 223. The flange 232 of the prior embodiment has a generally flat outer surface which generally coincides with and merges tangentially into the outer surface of the central body 222 of the shell. This presents a rather large, flat retractor-engaging surface which helps hold the shield 210 in a fixed orientation with respect to a relatively flat retractor blade. The shield 210' of FIGS. 24–26, however, has a flange 232' which extends downwardly and outwardly from the central body 222' and terminates at an elongate lip 228.

When this shield 210' is used with a flat-bladed retractor, the flange 232 will first contact the blade. Since the lip is positioned beneath and outwardly away from the central body 222' and the tissue-receiving channel 270', the device will tend to rotate in response to urging of the retractor, with the outer edges of the legs 224' and 228' pivoting upwardly. As a consequence, more of the retraction force will be borne by the underside of the tissue within the channel 270' than on top. Providing a longer lower leg 228' provides more surface area to distribute this force.

The upper leg 224' carries a manually graspable handle 223 extending upwardly from an upper surface therefrom. This handle makes it easier for a physician to insert the shield 210' into position within an incision and to retract the shield when the procedure is complete. If so desired, a depression in the upper surface of the upper leg 224' can be positioned on either side of the handle to make it even easier for the physician to grasp the handle. While the handle in FIGS. 24–26 is shown as a simple flat projection, it should be understood that other shapes can be employed to better facilitate the physician's grasp on or control over the device.

As noted previously, the shell (20, 120, 220 or 220', depending on which embodiment is used) is adapted to mechanically engage a surgical retractor. In each of the illustrated embodiments, the shell may simply abut a blade of a retractor without being attached thereto. In an alternative embodiment of the invention (not shown), this mechanical engagement may comprise a mechanical connection between the retractor and the shield such that the shield effectively comprises the blade of the retractor rather than an adjunct for use therewith. It is currently believed that a pivotable connection between the retractor and the shield is preferable so the shield may pivot to transfer the retraction force as intended despite rotation of the tissue or underlying structure (e.g., a rib) therein as the incision is widened. Each of the illustrated embodiments, however, provides a simple, cost-effective device which can be used advantageously with most surgical retractors already on the market. This permits a physician to continue using a surgical retractor with which he or she is already familiar or already has on-hand rather than having to switch to a new retractor to gain the benefits of this invention.

While a preferred embodiment of the present invention has been described, it should be understood that various changes, adaptations and modifications may be made therein without departing from the spirit of the invention and the scope of the appended claims.

What is claimed is:

1. A tissue compression shield comprising a shell having a rigid outer surface adapted to mechanically engage a surgical retractor and a concave inner surface defining an elongate tissue-receiving channel, the concave inner surface being adapted to deform under localized pressure to increase surface area in contact with tissue within the channel, thereby more widely distributing pressure across the tissue.

2. The tissue compression shield of claim 1 wherein the shell carries a compressible inner pad which defines at least a portion of the concave inner surface, the pad being formed of a compressible polymeric material which so deforms under localized pressure.

3. The tissue compression shield of claim 1 wherein the shell is generally U-shaped in cross section and has a central body and a pair of opposed legs extending away from the central body, the central body being more rigid than at least one of said legs.

4. The tissue compression shield of claim 3 wherein the central body and said at least one leg comprise the same material, the thickness of said material in the central body being greater than the thickness of said material in at least a portion of said at least one leg.

5. A tissue compression shield comprising:
   a) a rigid outer shell having an outer surface adapted to abut a surgical retractor and having a concave inner surface defining an elongate tissue-receiving channel; and
   b) a compressible inner pad carried on the inner surface of the outer shell within the tissue-receiving channel, the inner pad being adapted to deform under localized pressure to increase surface area in contact with tissue within the channel, thereby more widely distributing pressure across the tissue.

6. The tissue compression shield of claim 5 wherein the inner pad comprises a polymeric material having a hardness less than the hardness of the material of which the outer shell is formed.

7. The tissue compression shield of claim 5 wherein said hardness of said inner pad is no more than about 30 Shore A.

8. The tissue compression shield of claim 5 wherein the tissue-receiving channel is generally concave and is sized to receive a patient's rib therein.

9. The tissue compression shield of claim 5 wherein the outer shell is generally U-shaped in cross section and has an central body and a pair of opposed legs extending away from the central body, the central body being stronger than at least one of the legs.

10. The tissue compression shield of claim 9 wherein the central body of the outer shell is thicker in cross section than is said at least one leg.

11. The tissue compression shield of claim 5 wherein the inner pad extends along a majority of the length of the tissue-receiving channel.

12. The tissue compression shield of claim 11 wherein the outer shell is generally U-shaped in cross section and has a central body and a pair of opposed legs extending away from the central body.

13. The tissue compression shield of claim 12 wherein the inner pad is carried by the central body of the outer shell.

14. The tissue compression shield of claim 13 wherein each of the legs of the outer shell has an outer edge disposed away from the central body thereof, the inner pad being spaced inwardly of the outer edge of at least one of the legs.

15. The tissue compression shield of claim 5 wherein the outer shell has a central body and a pair of opposed legs extending away from the central body, at least one of the legs having a varying flexibility, with flexibility of said at least one leg being less adjacent the central body than adjacent an outer edge thereof.

16. A tissue compression shield comprising:
   a) a shell having a concave inner surface defining an elongate tissue-receiving channel which has a width and is open along a first side of the shell, the concave inner surface being compressible and adapted to deform under localized pressure; and
   b) a retractor-engaging surface carried by the shell on a second side opposite the first side, the surface extending laterally beyond the width of the channel on at least one side of the channel.

17. The tissue compression shield of claim 16 wherein the retractor-engaging surface comprises a surface of a flange which depends downwardly from the shell's body.

18. The tissue compression shield of claim 17 wherein the flange is formed integrally with the shell.

19. The tissue compression shield of claim 17 wherein the shell has a transverse length and the flange extends along a majority of said transverse length.

20. A tissue compression shield comprising a shell having a central body and a pair of opposed legs extending outwardly away from the central body, the central body and the opposed legs defining therebetween an elongate tissue-receiving channel, an upper one of the legs having a notch extending along an outer edge thereof, the notch defining a bone-seating recess, the recess being smaller than the tissue-receiving channel.

21. The tissue compression shield of claim 20 further comprising a compressible inner pad carried on the inner surface of the outer shell within the tissue-receiving channel, the inner pad being adapted to deform under localized pressure to increase surface area in contact with tissue within the channel, thereby more widely distributing pressure across the tissue.

22. The tissue compression shield of claim 20 wherein the notch extends along a majority of the length of said leg outer edge, thereby defining an elongate bone-seating recess.

23. The tissue compression shield of claim 20 wherein the shell includes a plurality of said notches spaced from one another along said leg outer edge.

24. A surgical retraction system comprising a retractor and a tissue compression shield,
   a) the retractor having a pair of engagement surfaces operatively linked to one another to permit a user to selectively urge the engagement surfaces away from one another to spread an incision made in tissue; and
   b) the tissue compression shield having a shell having a rigid outer surface in mechanical engagement with at least one of the retractor's engagement surfaces and a concave inner surface defining an elongate tissue-receiving channel, the concave inner surface being adapted to deform under localized pressure to increase surface area in contact with tissue within the channel, thereby more widely distributing pressure across the tissue.

25. A surgical retraction system comprising a retractor and a tissue compression shield,
   a) the retractor having a pair of engagement surfaces operatively linked to one another to permit a user to selectively urge the engagement surfaces away from one another to spread an incision made in tissue; and
   b) the tissue compression shield having a rigid outer shell and a compressible inner pad,
      i) the outer shell having an outer surface in compressive engagement with at least one of the retractor's engagement surfaces and having a concave inner surface defining an elongate tissue-receiving channel; and
      ii) the inner pad being carried on the inner surface of the outer shell within the tissue-receiving channel, the inner pad being adapted to deform under localized pressure to increase surface area in contact with tissue within the channel, thereby more widely distributing pressure across the tissue.

26. A method of retracting a patient's tissue, comprising:
   a) providing a tissue compression shield having a shell having a rigid outer surface and a compressible, concave inner surface defining a tissue-receiving channel;

b) placing the tissue compression shield within an incision in the patient's tissue, tissue on one side of the incision being received within the channel and contacting the compressible inner surface; and c) spreading the incision by urging against the outer surface of the tissue compression shield, thereby urging the inner surface outwardly against the tissue within the channel and causing the compressible inner surface to compress such that it deforms to better conform to a surface of the tissue within the channel, thereby more widely distributing pressure across the tissue.

* * * * *